(12) United States Patent
Goldson et al.

(10) Patent No.: US 9,567,622 B2
(45) Date of Patent: *Feb. 14, 2017

(54) ISOTONIC BUFFERED COMPOSITION AND METHOD THAT ENABLES COUNTING OF CELLS

(71) Applicant: Beckman Coulter, Inc., Brea, CA (US)

(72) Inventors: Wayne Goldson, Weston, FL (US); Sandra Socarras, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/730,963

(22) Filed: Jun. 4, 2015

(65) Prior Publication Data

US 2016/0002698 A1    Jan. 7, 2016

Related U.S. Application Data

(62) Division of application No. 12/853,046, filed on Aug. 9, 2010, now Pat. No. 9,091,677.

(51) Int. Cl.
    *C12Q 1/06*     (2006.01)
    *G01N 33/50*    (2006.01)
    *C12Q 1/02*     (2006.01)

(52) U.S. Cl.
    CPC ............. *C12Q 1/06* (2013.01); *G01N 33/5002* (2013.01)

(58) Field of Classification Search
    CPC ............... C12Q 1/06; C12Q 1/04; C12Q 1/02; C12Q 1/00; Y10T 436/11; Y10T 436/00; G01N 33/5002; G01N 33/50; G01N 33/48; G01N 33/00
    USPC .......................................... 435/29, 4; 436/43
    See application file for complete search history.

(56) References Cited

U.S. PATENT DOCUMENTS

| | | |
|---|---|---|
| 3,549,994 A | 12/1970 | Rothermel et al. |
| 3,847,545 A | 11/1974 | Shanbrom et al. |
| 3,874,852 A | 4/1975 | Hamill |
| 3,962,125 A | 6/1976 | Armstrong |
| 4,346,018 A | 8/1982 | Carter et al. |
| 4,384,971 A | 5/1983 | Carter et al. |
| 4,485,175 A | 11/1984 | Ledis et al. |
| 4,506,018 A | 3/1985 | North, Jr. |
| 4,521,518 A | 6/1985 | Carter et al. |
| 4,528,274 A | 7/1985 | Carter et al. |
| 4,882,284 A | 11/1989 | Kirchanski et al. |
| 4,962,038 A | 10/1990 | Carter et al. |
| 5,185,264 A | 2/1993 | Makela |
| 5,227,304 A | 7/1993 | Wong |
| 5,250,438 A | 10/1993 | Ryan |
| 5,389,549 A | 2/1995 | Hamaguchi et al. |
| 5,510,267 A | 4/1996 | Marshall |
| 5,639,630 A | 6/1997 | Malin et al. |
| 5,654,262 A | 8/1997 | Desai et al. |
| 5,786,224 A | 7/1998 | Li et al. |
| 5,817,518 A | 10/1998 | Li et al. |
| 5,888,752 A | 3/1999 | Malin et al. |
| 5,895,645 A | 4/1999 | Dabrowski et al. |
| 5,935,857 A * | 8/1999 | Riesgo ............... G01N 33/5002 252/408.1 |
| 5,939,326 A | 8/1999 | Chupp et al. |
| 6,025,201 A | 2/2000 | Zelmanovic et al. |
| 6,225,124 B1 | 5/2001 | Houwen et al. |
| 6,406,915 B2 | 6/2002 | Ryan et al. |
| 6,468,732 B1 | 10/2002 | Malin et al. |
| 6,509,192 B1 | 1/2003 | Young |
| 6,524,858 B1 | 2/2003 | Zelmanovic et al. |
| 6,573,102 B2 | 6/2003 | Li et al. |
| 6,579,688 B2 | 6/2003 | Steaffens et al. |
| 6,632,676 B1 | 10/2003 | Crews et al. |
| 6,673,627 B2 | 1/2004 | Tyrrell et al. |
| 6,706,526 B2 | 3/2004 | Lang et al. |
| 6,723,563 B2 | 4/2004 | Ryan |
| 6,869,798 B2 | 3/2005 | Crews et al. |
| 7,175,992 B2 | 2/2007 | Fong |
| 7,247,484 B2 | 7/2007 | Wu et al. |
| 7,279,136 B2 | 10/2007 | Takeuchi et al. |
| 7,324,194 B2 | 1/2008 | Roche et al. |
| 7,338,809 B2 * | 3/2008 | Yokoi ............... G01N 33/54393 422/400 |
| 9,091,677 B2 | 7/2015 | Goldson et al. |
| 2003/0166290 A1 | 9/2003 | Lang et al. |
| 2004/0014152 A1 | 1/2004 | Hendrikus |
| 2007/0104614 A1 | 5/2007 | Wang et al. |
| 2007/0238632 A1 | 10/2007 | Riesgo et al. |
| 2007/0269882 A1 | 11/2007 | Zhang et al. |
| 2008/0254543 A1 | 10/2008 | Ryan |
| 2008/0293144 A1 | 11/2008 | Guo |

FOREIGN PATENT DOCUMENTS

| | | |
|---|---|---|
| EP | 0582736 A1 | 2/1994 |
| WO | 97/19350 A1 | 5/1997 |
| WO | 2007/081387 A1 | 7/2007 |
| WO | 2012/021458 A1 | 2/2012 |

OTHER PUBLICATIONS

Banfi, G. et al, Evaluation of the Coulter Counter S-Plus VI, Journal of Automatic Chemistry, vol. 10, No. 1, Jan.-Mar. 1988, pp. 31-36.*
Galembeck et al., Effects of polyoxyethylene chain length on erythrocyte hemolysis induced by poly[oxyethylene (n) nonylphenol] non-ionic surfactants. Chemico-Biological Interactions, vol. 113, pp. 91-103 (1998).
International Search Report and Written Opinion mailed on Nov. 4, 2011 for International Application No. PCT/US2011/046965, filed on Aug. 8, 2011.
O'Neil et al., Performance evaluation of the complete blood count and white blood cell differential parameters on the AcT 5diff hematology analyzer. Laboratory Hematology, 7:116-124 (2001).
Ybertaud9 et al., ByzantineFlowers, Apr. 7, 2012, retrieved from the internet: http://ybertaud9.wordpress.com/2012/04/07/cilantropesto-removes-heavy -metals-health -benefits/.

* cited by examiner

*Primary Examiner* — Christine T Mui
(74) *Attorney, Agent, or Firm* — K&L Gates LLP; Louis C. Cullman; Georgia Kefallinos

(57) ABSTRACT

The present invention discloses multi-purpose metering fluid/rinse reagents for use in automated cellular analyzers that use liquid volumetric metering. The compositions contain a chelating agent, an ionizing salt, optionally a stabilizing ion, a buffer, a non-hemolytic surfactant, and optionally an antimicrobial agent. Advantageously, the compositions produce less than one part-per-million of formaldehyde over the course of one year. Methods for using the compositions are also described.

13 Claims, 1 Drawing Sheet

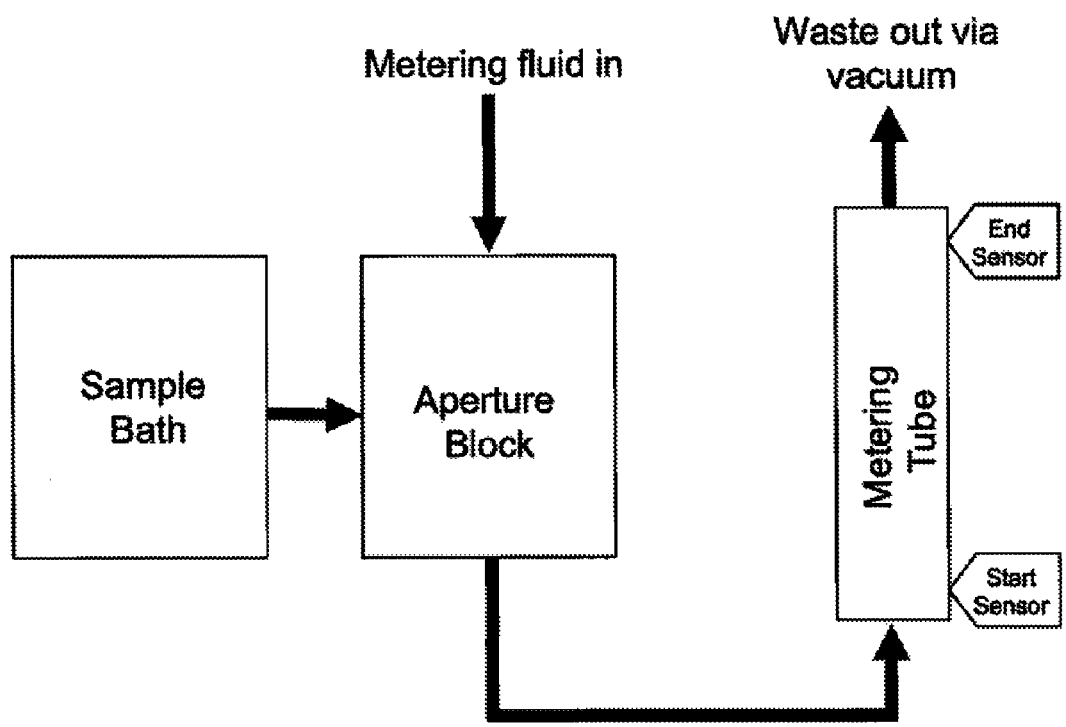

ISOTONIC BUFFERED COMPOSITION AND METHOD THAT ENABLES COUNTING OF CELLS

This application is a divisional of U.S. patent application Ser. No. 12/853,046 filed Aug. 9, 2010, the entire disclosure of which is incorporated herein by reference.

FIELD OF THE INVENTION

The present invention relates to a metering fluid composition for automated cellular analyzers that use liquid volumetric metering. The invention also relates to methods for controlling the start and stop of a counting episode on an automated cellular analyzer that uses liquid volumetric metering.

BACKGROUND

Automated cellular analyzers, such as hematology analyzers, enable the counting and characterization of cells in a cellular sample. Certain of these instruments detect changes in electrical conductance as cells are drawn through a small aperture. Cells conduct electricity differently than their surrounding fluid. Therefore, their passage through the aperture alters its effective cross-section and hence its conductivity. The accurate counting and characterization of cells by these devices requires the ability to precisely measure the volume of sample analyzed during a count episode. One way to do this is to utilize liquid volumetric metering, where the flow of a specific volume of a fluid through a capillary controls the start and stop of a counting episode.

The metering system of automated cellular analyzers that use liquid volumetric metering can comprise a metering tube, a start sensor, and an end sensor. The start sensor and the end sensor are located at opposite ends of the metering tube. Both sensors can be optical sensors, calibrated to detect a change in light intensity that occurs as the meniscus of the metering fluid passes. The flow of a liquid metering fluid through the metering tube, first past the start sensor and then past the end sensor, triggers the start and stop of a counting episode.

Presently, automated cellular analyzers that use liquid volume metering have the metering tube and sensors oriented vertically such that the start sensor is at the top of the metering tube and the end sensor is at the bottom of the metering tube. The metering fluid flows from the top down, first triggering the start sensor and then the end sensor. In this orientation, the problem of liquid "side flow" can occur. Due to the effects of gravity on the liquid metering fluid, some of the fluid can flow faster along a side of the inner wall of the metering tube, changing the angle of the meniscus such that it will not be detected by the start and stop sensors. In this case, metering fails. To combat this problem, metering fluids are designed with relatively high surface tensions that reduce the probability of side flow. However, even with a metering fluid with a relatively high surface tension, side flow can occur if cellular debris deposits on the metering tube.

Recently, automated cellular analyzers with liquid volumetric metering systems that eliminate the side flow problem have been designed. These instruments use a metering tube oriented vertically, but the metering fluid flows from the bottom up. The start sensor is located at the bottom of the metering tube and the end sensor is located at the top of the metering tube. Thus, the side flow phenomenon is completely eliminated as the effects of gravity on the metering fluid are no longer relevant. The development of these instruments necessitated the development of novel metering reagents, as existing reagents were not suitable for use in these new systems.

Automated cellular analyzers are often arranged such that on one side of the aperture is a sample bath which receives the cellular sample suspended in an isotonic diluent prior to analysis. On the other side of the aperture is a rinse reagent that acts to flush cells away from the aperture after they have been counted. The rinse reagent is in fluid communication with the sample bath, and as such, back flow can occur wherein some of the rinse reagent enters the sample bath and comes into contact with the cellular sample. This is especially so when the instrument is not in use. Traditionally, the isotonic diluent used to suspend the cellular sample is also used as the rinse reagent. Thus, the fluids on either side of the aperture are traditionally the same.

Many of the commercially available metering fluids and rinse reagents for use in automated cellular analyzers produce formaldehyde in amounts in excess of about 400 parts per million. Formaldehyde has been classified as a known human carcinogen by the WHO International Agency for Research on Cancer (IARC), and is also toxic and allergenic. Increasingly, regulatory agencies in states like California and Massachusetts have been restricting the amount of formaldehyde allowed in industrial and medical waste. According to these regulations, formaldehyde concentrations in waste equal to or less than 1 part-per-million is considered formaldehyde-free. Consequently, diluents, metering fluids, and rinse reagents for use in automated cellular analyzers that produce less than 1 part-per-million (ppm) of formaldehyde over the course of their shelf-life are highly desirable.

The present invention improves upon the metering fluids currently available by disclosing stable metering fluids optimized for use in automated cellular analyzers that use a bottom-up metering tube arrangement. The metering fluids of the present invention have a relatively low surface tension and detergent capabilities that aid in preventing the deposition of cellular debris on the inner surfaces of the instrument, simplifying the cleaning and maintenance of the cellular analyzer. The metering fluids of the present invention are also isotonic and non-hemolytic, and thus are suitable for use as a rinse reagent. In contrast to the diluents traditionally used as rinse reagents, the compositions of the present invention have detergent capabilities. Thus, when also used as the rinse reagent, the metering fluids of the present invention aid in preventing the deposition of cellular debris in and around the aperture.

The metering fluids of the invention can also be used to flush out the cellular analyzer in between count episodes to remove cellular debris on the inner surfaces of the instrument. The metering fluid compositions of the present invention preferably also have broad biocidal activity, are isotonic, non-hemolytic, and produce menisci with angles that properly trigger the start and end sensors, beginning and ending the counting interval. Advantageously, the metering fluid compositions of the present invention also produces less than about 1 part-per-million of formaldehyde over the course of their shelf lives.

BRIEF SUMMARY OF THE INVENTION

The present invention is directed toward non-hemolytic compositions to be used in automated cellular analyzers that use liquid volumetric metering. In certain embodiments, the compositions comprise a chelating agent, an ionizing salt, and a non-hemolytic surfactant.

In certain embodiments, the composition for use in an automated cellular analyzer that uses liquid volumetric metering, comprise: a) a chelating agent, b) an ionizing salt, and c) a non-hemolytic surfactant, wherein the composition is non-hemolytic, has a pH of about 6.5 to about 7.5, and wherein the surface tension of the composition is between about 40 dynes/cm and about 66 dynes/cm.

In certain embodiments, the composition for use in an automated cellular analyzer that uses liquid volumetric metering, comprise: a) a chelating agent, b) an ionizing salt, and c) a non-hemolytic surfactant, wherein the composition is non-hemolytic, has a pH of about 6.5 to about 7.5, and wherein the composition produces a meniscus with an angle between about 30° and about 60° in a borosilicate glass capillary with an internal diameter of 2.7 mm.

In certain embodiments, the compositions are in fluid communication with the automated cellular analyzer. Thus, for example, the metering fluids of the present invention can be stored in a large volume container fluidly connected to the automated cellular analyzer through a screw cap connector. The container can be configured such that it can be connected directly to the automated cellular analyzer.

The present invention is also directed toward methods for controlling the start and stop of a counting episode on an automated cellular analyzer that uses liquid volumetric metering.

In certain embodiments, the method for controlling the start and stop of a counting episode on an automated cellular analyzer that uses liquid volumetric metering comprises: providing to a metering tube a metering fluid composition comprising: a chelating agent, an ionizing salt, and a non-hemolytic surfactant; flowing the metering fluid composition through the metering tube; wherein the meniscus of the metering fluid first triggers the start sensor, beginning the counting episode, and then triggers the end sensor, stopping the counting episode. In certain embodiments, the method for controlling the start and stop of a counting episode on an automated cellular analyzer that uses liquid volumetric metering further comprises the step of placing the metering fluid composition in fluid communication with the sample bath.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

The FIGURE is a schematic diagram of the components of an automated cellular analyzer that uses liquid volume metering.

DETAILED DESCRIPTION OF THE INVENTION

Definitions

The phrase "low formaldehyde" as used herein and throughout this specification is meant to describe a solution having or producing less than about 1 part per million (ppm) of formaldehyde over a period of time of at least 1 year. In one embodiment, low formaldehyde describes a solution having or producing less than about 0.70 ppm of formaldehyde over a period of time of at least 1 year. In another embodiment, low formaldehyde describes a solution having or producing less than about 0.10 ppm of formaldehyde over a period of time of at least 1 year. In a preferred embodiment, low formaldehyde describes a solution having or producing less than about 0.01 ppm of formaldehyde over a period of time of at least 1 year. In other embodiments, low formaldehyde describes a solution having or producing less than about 0.001 ppm of formaldehyde over a period of time of at least 1 year.

Formaldehyde can be measured using EPA method 8315A. This method entails derivitizing the sample with 2,4-dinitrophenylhydrazine to convert the carbonyl groups of aldehydes present to the hydrazones. Each carbonyl compound present in the sample forms a separate hydrazone derivative and these individual derivatives are extracted from the solution using an organic solvent. The individual hydrazone derivatives are separated and quantified by HPLC (High Performance Liquid Chromatography). The details of EPA method 8315A can be obtained from the EPA website.

The term "surface tension" as used herein refers to the cohesive forces, such as Van der Waals forces, that draw liquid molecules together. In the bulk of a liquid, each liquid molecule is pulled equally in every direction by neighboring liquid molecules, resulting in a net force of zero. The surface of any liquid is an interface between that liquid and some other medium. At the surface of a liquid, the liquid molecules are in contact with other liquid molecules and also with the surface of the neighboring medium (be it another liquid, a gas, or a solid medium). Therefore, all of the molecules at the surface are subject to cohesive forces that attract them to other liquid molecules as well as to adhesive forces that attract or repel them to the molecules in the neighboring medium. The liquid will assume a geometry that balances these forces at the boundary.

Solutes can have an effect on the surface tension of a liquid. For example, inorganic salts tend to increase surface tension. Surfactants and alcohols will tend to decrease surface tension.

Surface tension can be measured in force per unit length as dynes per centimeter (dyne/cm) or in newtons per meter (mN/m). (1 dyne/cm=0.001 N/m). There are many known methods for determining the surface tension of a liquid. These include capillary meniscus measurement (J. E. Lane, J Colloid Interface Sci., 42, 145-149 (1973)), advancing and receding contact angle measurements of an immersed Wilhelmy plate (R. H. Dettre, R. E. Johnson, J Colloid Interface Sci., 21, 367 (1966)), the DuNouy ring method (W. D. Harkins, H. F. Jordan, J. Amer. Chem. Soc., 52, 1751 (1930)), and pendant drop shape analysis (K. Hansen, G. Rodsrun, J Colloid Interface Sci., 141, 1-12 (1991)). A commonly used technique for measuring surface tension is the capillary rise method. The capillary rise method involves immersing the end of a capillary into the solution to be measured. The height at which the solution rises inside the capillary is related to the surface tension by the equation $\gamma = \frac{1}{2}\rho h r g$, where $\gamma$ is the surface tension of the liquid, $\rho$ is the liquid density, h is the capillary rise, r is the radius of the capillary, and g is the acceleration due to gravity. The surface tension units discussed herein, unless otherwise stated, were measured using the capillary rise method.

As used herein, the term "meniscus" refers to the curve in the surface of a liquid that is produced as a result of the balancing of the cohesive forces between the liquid molecules and the adhesive forces between the liquid molecules at the liquid surface/solid surface interface and the solid surface. A meniscus can be concave, convex, or flat. A convex meniscus occurs when the liquid molecules have a stronger attraction to each other than to the solid surface. Conversely, a concave meniscus occurs when the molecules of the liquid attract those of the solid surface.

The angle of the meniscus (also known as the contact angle) is the angle at which the liquid/vapor interface meets the solid surface. The angle of the meniscus is specific for any given system and is determined by the cohesive and adhesive forces interacting across the three interfaces. The angle of a given meniscus can be measured using a contact angle goniometer. Alternatively, the angle of the meniscus can be calculated using Young's Equation: $\gamma^{sv}=\gamma^{sl}+\gamma^{lv}\cos\theta$, wherein $\gamma^{sv}$=the solid surface free energy, $\gamma^{sl}$=the solid/liquid interfacial free energy, $\gamma^{lv}$=the liquid surface free energy and $\theta$ is the angle of the meniscus.

As used herein, the terms "isotonic" or "iso-osmotic" refer to a solution that has about the same osmolality as the cell sample to be analyzed. A metering fluid that is too hypotonic (a lower osmolality than the cellular sample) can result in water diffusing into cells, which in turn will cause cells to swell and burst, releasing cellular debris that can accumulate on the inner surfaces of the instrument. A metering fluid that is too hypertonic (a higher osmolality than the cellular sample) can result in water diffusing out of the cells, which will cause cells to shrink. In certain embodiments, the cellular sample is blood. Physiological fluids such as blood can have osmolality values ranging from about 240 mOsm/kg to about 340 mOsm/kg. Thus, when physiological fluids are used as the cellular sample, an isotonic solution will have osmolality values ranging from about 240 mOsm/kg to about 340 mOsm/kg.

The term "antimicrobial agent" as used herein and throughout this specification is meant to describe any chemical compound that is effective in reducing or eliminating microorganisms including, but not limited to, gram positive bacteria, gram negative bacteria, fungi, and yeast.

The term "non-hemolytic" as used herein and throughout this specification is meant to describe a solution that will not cause the lysis of a significant number of cells in a cellular sample when the cells are exposed to the solution for the amount of time required to complete a count of the cellular sample on an automated cellular analyzer. Typically, a complete count cycle for an automated cellular analyzer is a minute or less. Thus, for example, a solution that does not lyse cells within about a minute of exposure thereto is non-hemolytic.

Automated cellular analyzers that use liquid volumetric metering of the present invention will have a metering system that comprises a metering tube, a start sensor, an end sensor, and a vacuum chamber. The start sensor and the end sensor are located at opposite ends of the metering tube. If the automated cellular analyzer has the metering tube in a bottom-up configuration, the metering tube will be arranged vertically with the start sensor located at the bottom of the metering tube and the end sensor located at the top of the metering tube. The top of the metering tube is in communication with the vacuum chamber. Applying a negative pressure inside the vacuum chamber will force a liquid metering fluid to flow up through the metering tube, first past the start sensor and then past the end sensor. The sensors are calibrated to detect the passage of the meniscus at the air/liquid/metering tube surface interface.

The start sensor and the end sensor are optical sensors designed to detect changes in light intensity. In certain embodiments, the start and end sensors are light-emitting diode (LED) sensors. When the metering fluid surface passes the start sensor, the presence of the meniscus of an appropriate angle causes a change in light intensity, and hence an electrical signal is generated, triggering the start of a count. When the metering fluid surface reaches the end sensor, the meniscus of the appropriate angle again causes a change in light intensity and hence another electrical signal is generated resulting in the termination of the count. An exemplary liquid volumetric device that uses a bottom-up metering system is disclosed in U.S. Patent Publication No. 2007/0269882 to Zhang et al., incorporated by reference herein in its entirety.

Thus, it is an object of the present invention to provide a low surface tension metering fluid for use in automated cellular analyzers that use a bottom-up metering system, and which produces a meniscus with an angle at the liquid/air/metering tube interface that results in the proper change in light intensity to trigger the beginning and end of the counting interval. As these reagents in some instances are stored for long periods of time before use, they preferably have suitable antimicrobial properties to prevent the growth of bacteria and fungi. It is also important to prevent microorganism growth inside the instruments, such as inside the metering tube, because organism growth can cause contamination of the instrument components and interfere with system performance. For example, microorganisms can be mistakenly counted as a sample cell, obscuring the results of the count. Thus, it is preferable for a metering fluid to have effective antimicrobial activity.

A cellular sample will often contain proteins and debris from lysed cells. These materials can precipitate on the surface of instrument components that are in contact with the sample mixtures. Furthermore, these materials can also form insoluble complexes with chemicals in the diluent, precipitating on the surface of the instrument components. Over time, these precipitates can build up, causing partial or complete clogging of the aperture or metering tube, potentially rendering the instrument inoperable or causing erroneous cell counts. Thus, rinse reagents for use in automated cellular analyzers that 1) are non-hemolytic and isotonic, and, 2) have detergent capabilities which aid in the removal of precipitated cellular proteins and debris from the inner surfaces of the instrument, are particularly desirable.

Thus, it is a further object of the present invention to provide metering fluid reagents that can also be used as rinse reagents. The metering fluids of the present invention are isotonic, non-hemolytic, and have a low surface tension and detergent capabilities. Thus, the metering fluids of the present invention are superior rinse reagents compared to traditionally used rinse reagents because they will aid in preventing the deposition of cellular debris in and around the aperture. This will reduce the need for a separate reagent for cleaning the instrument and thus reduce the cost of operation, increase the accuracy and consistency of the cellular counts, and increase the time between routine maintenance and cleaning of the instrument. The compositions of the present invention can also be frozen and thawed without the loss of efficacy. Additionally, the compositions of the present invention produce less than 1 ppm of formaldehyde over the course of one year.

Chelating Agents

The composition of the present invention contains one or more chelating agents as a component. A chelating agent is a compound that chelates ions in cell membranes and weakens them, making the cell more susceptible to biocides. Thus, the chelating agent assists the antimicrobial compounds in the composition in killing bacteria and fungi. The chelating agent can also work in conjunction with the buffer to maintain the pH of the composition. In the case where the cellular sample is a blood sample, the chelating agent also helps to maintain anticoagulation of the blood by reducing platelet aggregation.

In one embodiment, the chelating agent can be ethylenediamine tetraacetic acid (EDTA), an EDTA derivative, or combinations thereof. In one specific embodiment, the chelating agent is an EDTA derivative. EDTA derivatives include salts of EDTA, such as disodium EDTA, tetrasodium EDTA, dipotassium EDTA, and ethyleneglycol-bis-(3-aminoethylether)N—N'-tetraacetic acid (EGTA). For example, in an embodiment, the chelating agent is disodium EDTA. In another embodiment, the chelating agent is dipotassium EDTA. In still another embodiment, the chelating agent is ethyleneglycol-bis-(2-aminoethyl ether)N,N,N',N'-tetraacetic acid (EGTA).

In another embodiment, additional chelating agents other than EDTA or its derivatives can be added to the composition of the present invention. Such additional chelating agents include compounds that chelate ions as described above, which are known to those skilled in the art. Some of these chelating agents include, without limitation, cyclohexanediamine-tetraacetic acid, diethylentriaminepentaacetic acid, and/or hydroxyethylethylene-diaminetriacetic acid.

The concentration of each chelating agent in the composition is typically present from about 0.05 grams per liter (g/L) to about 6.0 g/L. In certain embodiments, the concentration of each chelating agent in the composition is from about 2 g/L to about 4 g/L. Preferably, the concentration of the chelating agent is from about 2.7 g/L to about 3.3 g/L.

Stabilizing Ions

The composition of the present invention preferably contains one or more stabilizing ions as a component. The stabilizing ions contribute to the isotonicity, osmolality, and ionic strength of the composition, contribute to the conductivity of the solution, and assist in maintaining electrochemical balance. The stabilizing ions also assist in solubilizing abnormal proteins in the sample and prevent them from precipitating. Preferably, the stabilizing ions include a sulfate anion. The sulfate anion can be provided by a sulfate salt such as an alkali metal sulfate salt. Exemplary alkali metal sulfate salts include, but are not limited to, sodium and potassium sulfates. Preferably, the alkali metal sulfate salt is sodium sulfate. In one embodiment, the alkali metal sulfate is added to the composition as an aqueous solution. Preferably, the stabilizing ion is present in the composition at a concentration of about 7 g/L to about 21 g/L. More preferably, the stabilizing ion is present in the composition at a concentration of about 12 g/L to about 16 g/L.

It is also contemplated that stabilizing ions can be provided by salts such as ammonium sulfate, sodium sulfate, magnesium acetate, guanidinium sulfate, and neutral salts containing citrate, acetate, and phosphate.

Ionizing Salts

The composition of the present invention contains one or more ionizing salts as a component. The ionizing salt assists the sulfate salt in regulating the osmolality and ionic strength of the composition. Preferably, the ionizing salt is an alkali metal chloride. Alkali metal chlorides include, but are not limited to, sodium and potassium chlorides. More preferably, the ionizing salt is sodium chloride. In one embodiment, the ionizing salt is added to the composition as an aqueous solution. Preferably, the ionizing salt is present at a concentration of about 0.1 g/L to about 5 g/L. More preferably, the ionizing salt is present at a concentration of about 0.5 g/L to about 1.5 g/L.

Buffers

The desired pH of the composition depends upon the cellular analysis instrument utilized and the test to be performed. Preferably, the pH of the composition is between about 5.0 to about 9.0. More preferably, the pH of the composition is between about 6.0 to about 8.5. Even more preferably, the pH of the composition is between about 6.2 to about 8.2. Even more preferably, the pH of the composition is between about 6.5 to about 7.5.

Generally, one or more buffers are added in the composition at concentrations sufficient to achieve the desired pH. This concentration is dependent on the concentration of other solutes that can contribute to the overall acidity or basicity of the composition.

For case of reference, this specification will use the term "buffer" or "a buffer". However, it is to be understood that two or more buffers can be used as the buffer for the present invention. The buffer is added to the composition in an amount sufficient to adjust the pH to the preferred range. Adjustment of the amount of the buffer to provide a suitable pH is an established approach. In certain embodiments, the buffer comprises a base. Preferably, the base is an alkali metal hydroxide. More preferably, the alkali metal hydroxide is sodium hydroxide or potassium hydroxide. Other bases can be utilized provided that they do not interfere with the analysis of the cellular sample. In one embodiment, the base is added as an aqueous solution. In another embodiment, the base is added as an aqueous 50% solution.

Surfactants

The composition of the present invention can additionally contain a non-hemolytic surfactant. The surfactant acts to lower the surface tension of the composition such that a meniscus with an angle that will trigger the start and stop sensors is formed between the surface of the metering fluid and the interior surface of the metering tube. Surfactants interfere with the ability of the molecules of a substance to interact with one another and, thereby, lower the surface tension of the substance. The surfactant also imparts detergent capabilities to the composition, giving it the ability to remove cellular debris and proteins that have precipitated onto the interior surfaces of the automated cellular analyzer and/or prevent the deposition of cellular debris and proteins. Preferably, the surfactant imparts freeze/thaw capabilities to the composition, allowing it to be stored in a frozen state and subsequently thawed for use without loosing effectiveness. The surfactant should also be stable in a high electrolyte environment and not precipitate out of solution. The surfactant should also be non-hemolytic, so that it can come into contact with erythrocytes and not cause them to lyse, which would result in cellular debris and the release of proteins that could contaminate the interior surfaces of the cellular analyzer and/or block the aperture.

Suitable non-hemolytic surfactants include, but are not limited to, polyethoxylated nonyl phenol (IGEPAL® CO-630, available from GAF Corp., also known as 2-[2-(4-nonylphenoxy) ethoxy]ethanol, CAS #9016-45-9), dodecyl nonaethylene glycol ether (polidocanol or TWEEN® 20, CAS #9002-92-0), ethoxylated monododecyl ether (THESIT®, available from Sigma Aldrich Co., CAS #9006-65-9), and ethoxylated dimethylsiloxane (SILWET® 7600, available from GE Silicones).

Surfactant(s) can be used at concentrations of about 0.1 g/L to about 3.0 g/L. Preferably, the concentration of surfactant(s) is about 0.5 g/L to about 2.5 g/L. Most preferably, the concentration of surfactant(s) is about 0.9 g/L to about 2.1 g/L.

Surface Tension

A critical parameter of the compositions of the invention is the surface tension. In order to form a meniscus with an angle that can be detected by the start and stop sensors, the surface tension must be properly adjusted. Components of the metering fluid, such as the ionizing salts, can contribute to the overall surface tension of the composition. The addition of a surfactant will lower the surface tension by interfering with the cohesive forces among the molecules of the composition.

In certain embodiments, the surface tension of the metering fluid of the present invention is between about 40 dynes/cm and about 66 dynes/cm. In certain embodiments, the surface tension is between about 47 dynes/cm and about 64 dynes/cm. In preferred embodiments, the surface tension is between about 52 dynes/cm and about 62 dynes/cm. One can adjust the concentration of the surfactant to achieve a surface tension that will result in a meniscus of an angle sufficient to be detected by the sensors as calibrated on an automated cellular analyzer that uses liquid volume metering. While the presence of solutes in the composition (such as sodium chloride and sodium sulfate) will have an effect on the surface tension, this effect is negligible compared to the effect of the surfactant.

Antimicrobials

Compositions for use in automated cellular analyzers can be stored for extended periods of time before use, and can often be exposed to microorganisms during use. Thus, the composition of the present invention preferably exhibits antimicrobial effectiveness, since the presence of microorganism contamination can distort the analysis of the cellular sample. Antimicrobial agents should be utilized to eliminate growth of microorganisms prior to and during analysis. However, antimicrobial agents used in the compositions known in the art have been found by the inventors to contribute to the production of formaldehyde levels greater than 1 ppm. For use in the composition of this invention, antimicrobial agents should have the following characteristics: In association with other components of the composition, these reagents should produce little or insubstantial amounts (e.g., preferably, less than 1 ppm) of formaldehyde for at least one year. The reagents should also provide adequate antimicrobial protection and yet not interfere with the measurement of the cellular sample in the various analytical procedures. Preferably, the antimicrobial agents do not react with other reagents conventionally used in many methods of cellular analysis.

The composition of the invention thus optionally contains one or more antimicrobial agents which are effective in eliminating gram negative bacteria, gram positive bacteria, yeast, and fungi, and yet which produce in the composition less than 1 ppm formaldehyde over the course of a year. Preferably, the antimicrobial agents useful in the composition of the invention include various combinations of 1,2-benzisothiazolin-3-one, 5-chloro-2-methyl-4-isothiazolin-2-one, 2-methyl-4-isothiazolin-3-one, and 5-bromo-5-nitro-1,3-dioxane, 4-butylaminobenzoicacid-2-(dimethylamino)ethylester hydrochloride, diazolidinyl urea, 1,2 dibromo-2,4 dicyanobutane, derivatives of each of these compounds, and combinations thereof. These antimicrobial agents are commercially available.

When employed in combination in the metering fluid composition of this invention, these antimicrobial compounds can be employed in any ratio effective to combat microbial growth throughout the shelf-life of the composition, without producing formaldehyde, and further without adversely affecting the cellular sample or cellular parameter to be measured by the selected analytical procedure.

Antimicrobials should be used in the composition of the invention at concentrations effective to combat microbial growth throughout the shelf-life of the composition. Effective concentrations of antimicrobials can be readily determined and will vary depending upon the choice of antimicrobial. In general, antimicrobials can be used in the composition of the invention at concentrations of about 0.1 g/L to about 2.0 g/L. In other embodiments, antimicrobials can be used in the composition of the invention at concentrations of about 0.5 g/L to about 1.5 g/L. In preferred embodiments, antimicrobials can be used in the composition of the invention at concentrations of about 0.5 g/L to about 1.0 g/L.

Certain antimicrobials, such as 4-butylaminobenzoicacid-2-(dimethylamino)ethylester hydrochloride, are effective at lower concentrations than those described above. Thus, in certain embodiments, such antimicrobials can be used in the composition of the invention at concentrations of about 0.01 to about 0.5 g/L. In other embodiments, such antimicrobials can be used in the composition of the invention at concentrations of about 0.01 g/L to about 0.1 g/L. In other such embodiments, antimicrobials can be used in the composition of the invention at concentrations of about 0.01 g/L to about 0.03 g/L.

It is anticipated that other antimicrobials can be similarly useful in compositions of this invention. Selection of such useful antimicrobial components following the teachings contained herein is encompassed by this invention. Methods for determining the suitability of a particular antimicrobial agent in the composition of the present invention are found in U.S. Pat. No. 6,706,526 B2, incorporated by reference herein in its entirety.

Other Components

The composition of the present invention can further contain other components including preservative agents, anticoagulants, detergents, dyes, and stains. See, for example, U.S. Pat. Nos. 5,935,857 and 4,528,274. However, any additional compounds added to the composition must not increase the formaldehyde production of the reagent. To the extent that such other components adversely impact the physical parameters of the cells to be analyzed, other adjustments to the composition formulation can be made to counteract these effects.

Osmolality

Generally, the metering fluid of the present invention will be iso-osmotic with respect to the cellular sample, usually a blood sample, so that the volumes of the cells in the cellular sample do not change. Normal adult blood osmolality is about 285 mOsm/kg to about 295 mOsm/kg. Abnormal blood osmolality can range from about 240 mOsm/kg to about 340 mOsm/kg. Preferably, the osmolality of the composition is between about 240 mOsm/kg to about 340 mOsm/kg. More preferably, the osmolality will be between about 260 mOsm/kg to about 320 mOsm/kg. Most preferably, the osmolality will be from about 280 mOsm/kg to about 290 mOsm/kg. However, the osmolality of the composition can vary when used it is with a cellular sample other than blood. Adjusting the osmolality of the composition by altering the concentration of the ionizing salt and the sulfate salt is routine.

Methods of Using the Metering Fluid Composition

Automated cellular analyzers that use liquid volumetric metering comprise a metering tube (usually a glass capillary), a start sensor, an end sensor, and a vacuum chamber. The automated cellular analyzers further comprise metering fluid and other reagents fluidly connected to the cellular analyzer. Thus, for example, fluidly connected to the cellular analyzer are fluid reservoirs or fluid reagent containers, at least one of which contains the metering fluid of the present invention.

In at least certain embodiments, the metering fluid of the present invention is stored in a large volume sterilized container. Preferably, such containers are large volume plastic (generally low density polyethylene) containers. Generally, the containers used for the present invention will hold at least 1 liter and more preferably 5 liters of the metering fluid. The containers are preferably sterilized and contain a vacuum seal to maintain sterility during storage.

In an especially preferred embodiment, the container is a 5 liter cube comprising low density polyethylene. The container further comprises an induction sealed cap with a mylar lining, which forms a breakable seal during the filling of the container with metering fluid of the present invention.

As previously mentioned, the container holding the metering fluid comprises a cap. In certain embodiments, the cap is 38 mm in diameter. The cap is removed and the mylar lining is either removed or punctured such that a male connector associated with the automated cellular analyzer can be connected to the container. The male connector further comprises, in a preferred embodiment, a pick up tube, which is of sufficient length to fit substantially within the container and preferably rests at or near the bottom of the metering fluid container.

As shown in the FIGURE, the start sensor and the end sensor are located at opposite ends of the metering tube. The end of the metering tube with the end sensor is in communication with the vacuum chamber. The end of the metering tube with the start sensor is in communication with an aperture block where the metering fluid is introduced into the device. In order to accurately dictate the start and stop point in a counting interval, a negative pressure is applied inside the vacuum chamber, forcing the metering fluid to flow out of the aperture block and then through the metering tube, first past the start sensor and then past the end sensor. The start and end sensors are calibrated to detect the passage of the meniscus at the air/liquid/metering tube surface interface. An exemplary liquid volumetric device is disclosed in U.S. Patent Publication No. 2007/0269882 to Zhang et al.

When the surface of the metering fluid passes the start sensor, the presence of the meniscus of the appropriate angle causes a change in light intensity that is detected by the sensor, and hence an electrical signal is generated, triggering the start of a counting episode. When the liquid surface reaches the end sensor, the meniscus of the appropriate angle again causes a change in light intensity that is detected by the end sensor and hence another electrical signal is generated resulting in the termination of the counting episode.

It is critical for the metering fluid/metering tube/air interface to create a meniscus that can be detected by the sensors in the particular cellular analyzer being used. The surface tension of the metering fluid, the internal diameter of the metering tube, as well as the material the metering tube is composed of all contribute to the angle of the meniscus. The metering fluid composition of the exemplified embodiment is designed to be used in a glass metering tube with an internal diameter of about 2.7 mm. However, it is understood that changes to the diameter of the metering tube, or even the composition of the tube itself, may require a change in the metering fluid composition to achieve the desired meniscus angle.

Thus, the compositions of the present invention are useful in methods for controlling the start and stop of a counting episode on an automated cellular analyzer that uses liquid volumetric metering. This method comprises: providing to a metering tube a non-hemolytic metering fluid composition comprising: a chelating agent, an ionizing salt, a non-hemolytic surfactant, and, optionally, a sulfate salt and/or one or more antimicrobial agents, wherein the composition is non-hemolytic, has a pH of about 6.5 to about 7.5, and wherein the surface tension of the composition is between about 40 dynes/cm and about 66 dynes/cm; flowing the metering fluid composition through the metering tube; wherein the meniscus of the metering fluid first triggers the start sensor, beginning the counting episode, and then triggers the end sensor, stopping the counting episode.

In addition to their use as metering fluids in methods for controlling the start and stop of a counting episode, the compositions of the present invention are useful as rinse reagents in methods to flush cells away from the aperture after they have been counted. Thus, the terms "metering fluid" and "rinse reagent" are herein used interchangeably when describing the compositions of the present invention. When used as a rinse reagent, the start and stop sensors are generally not turned on.

As discussed above, cellular analyzers are often arranged such that the cellular sample suspended in a diluent is contained in a sample bath on one side of the aperture. On the other side of the aperture is a rinse reagent that acts to flush cells away from the aperture after they are counted. The rinse reagent is in fluid communication with the sample bath, thus, back flow can occur wherein some of the rinse reagent enters the sample bath. As a cellular sample enters the sample bath, any residual rinse reagent can come into contact with the cellular sample. Therefore, the rinse reagent is non-hemolytic. Lysing of cells in the cellular sample can lead to cellular debris clogging the aperture, rendering the instrument inoperable, or resulting in erroneous cell counts. The metering fluids of the present invention are isotonic and non-hemolytic, and thus are suitable for use as rinse reagents. The non-hemolytic surfactants used in the metering fluids of the present invention also impart detergent capabilities, which aid in preventing deposition of cellular debris in and around the aperture. Therefore, the metering fluids of the present invention are useful in methods to prevent the deposition of cellular debris on the inner surfaces of cellular analyzers and in methods to improve the performance of cellular analyzers.

Even when the diluent and rinse reagent are non-hemolytic, cellular sample will often contain proteins and debris from lysed cells. These materials can precipitate on the surface of instrument components which are in contact with the sample mixtures during analysis. Furthermore, these materials can also form insoluble complexes with chemicals in the diluent, precipitating on the surface of the instrument components. Without an effective cleaning on a regular basis, these precipitates can build up, causing partial or complete clogging of the apertures or metering tube, potentially rendering the instrument inoperable. The metering fluid composition of the present invention has detergent capabilities, and therefore can also function as an effective reagent for cleaning cellular debris from the interior surfaces of automated cellular analyzers. The composition can be used to flush debris out of the interior surfaces of the device between analysis of cellular samples to unclog fluidic pathways and to remove contamination that can obscure the count and analysis of cells. The multi-purpose nature of the composition of the present invention reduces the number of reagents used on a particular cellular analyzer, simplifies operation, reduces the cost of analyzing each sample, and reduces the cost of maintenance.

EXAMPLES

The following examples are illustrative of the invention and are in no way to be interpreted as limiting the scope of the invention, as defined in the claims.

Example 1

A multipurpose metering fluid composition according to this invention is illustrated in Table 1, below:

TABLE 1

| Component | Quantity/L |
|---|---|
| disodium EDTA | 2.7-3.3 g |
| sodium sulfate | 12-16 g |
| sodium chloride | 0.5-1.5 g |
| polyethoxylated nonyl phenol | 0.7-1.3 g |
| antimicrobials | 0.1-2.0 g |
| 50% NaOH | 0.6 g |
| Water | Q.S. to 1.0 L |
| Final pH: 7.1-7.2; osmolality: 284 mOsm/kg | |

Example 2

A multipurpose metering fluid composition according to this invention is illustrated in Table 2, below:

TABLE 2

| Component | Quantity/L |
|---|---|
| disodium EDTA | 2.7-3.3 g |
| sodium sulfate | 12-16 g |
| sodium chloride | 0.5-1.5 g |
| dodecyl nonaethylene glycol ether | 1.6-2.4 g |
| antimicrobials | 0.1-2.0 g |
| 50% NaOH | 0.65 g |
| Water | Q.S. to 1.0 L |
| Final pH: 7.1-7.2; osmolality: 284 mOsm/kg | |

Example 3

The surface tensions of several commercially available reagents used in automated cellular analyzers (all available from Beckman Coulter, Inc., Brea, Calif.) and a metering fluid of the invention as described in Table 1, above, were measured using the capillary rise method. The results are presented in Table 3, below:

TABLE 3

| COULTER ® Reagent Tested | Surface Tension (dynes/cm) |
|---|---|
| Diluent I | 72.4 |
| Diluent II | 70.4 |
| Diluent III | 74.4 |
| Lytic Reagent I | 54.7 |
| Metering fluid composition from Table 1 | 57.4 |

Example 4

To assess the efficacy of a composition of the present invention as a metering fluid, control cell samples (COULTER® 4C®-ES Cell Control cells, Beckman Coulter, Inc.) were analyzed on the Mindray BC3000 cellular analyzer (Shenzhen Mindray BioMedical Electronics Co.) using the composition described in Table 1, above, as the metering fluid. The Mindray BC3000 is a 3 part differential hematology instrument that uses liquid volume metering.

4C®-ES Cell Control cells are a quality control product prepared from stabilized human blood cells, designed to confirm and monitor the accuracy of automated cellular analyzers. Three different types of 4C-ES Cell Control reagents are available: abnormal low white blood cell count (WBC), normal WBC (a normal WBC count is in the range of $4.3$-$10.8 \times 10^3$ cells/mm$^3$), and abnormal high WBC. All three types of control cells were used for this analysis. If the metering fluid does not properly trigger the start and stop of a counting episode, a "voteout" can occur. "Voteouts" occur when the automated cell analyzer software detects a disagreement among all count periods or the count does not meet internal criteria and the data are thrown out. When a voteout occurs, no data are gathered for that particular aspiration of the sample.

Two sample runs were performed with each cell sample, resulting in a total of six runs. Each run consisted of 20 aspirations of the cell sample. The number of aspirations in each run that resulted in a voteout was recorded. As a comparison, two commercially available reagents (Diluent I and II from table 3, above) were tested as metering fluids using the same protocol as described above. Each of these reagents was tested in one sample run and the number of aspirations that resulted in a voteout was recorded. The results are tabulated in Table 4, below:

TABLE 4

| Metering Fluid | Cell Sample | Run Number | Voteouts/Aspirations |
|---|---|---|---|
| Composition of the invention as described in Table 1 | Abnormal Low | 1 | 0/20 |
| | | 2 | 0/20 |
| | Normal | 1 | 0/20 |
| | | 2 | 0/20 |
| | Abnormal High | 1 | 0/20 |
| | | 2 | 0/20 |
| Diluent II | Abnormal Low | 1 | 2/3 |
| Diluent I | Normal | 1 | 7/20 |

The data above indicate that the composition of the invention as described in Table 1 is superior to the commercially available diluents as a metering fluid. In 6 runs using the composition of the invention as the metering fluid, not a single voteout occurred. As can be seen in the above tables, the commercially available diluents resulted in high rates of failure to trigger the start and stop points of the counting episode, resulting in voteouts. Thus, these reagents were deemed not suitable for use as a metering fluid. These results show that the surface tensions of the commercially available diluents are too high, and therefore these reagents do not create a meniscus with an angle that can be detected by the start and stop sensors.

Although the Lytic Reagent has a surface tension that will create a meniscus that can be detected by the start and stop sensors, it will also lyse cells, creating cellular debris that can precipitate on the inner surfaces of the cellular analyzer and result in poor performance. Thus, it is also not suitable for use as a metering fluid. The Lytic Reagent contains a quaternary ammonium salt as a lytic reagent and an alkali metal cyanide.

While various embodiments of the present invention have been described above, it should be understood that they have been presented by way of example, and not limitation. It will be apparent to persons skilled in the relevant arts that various changes in form and detail can be made therein without departing from the spirit and scope of the invention. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalence.

What is claimed is:

1. A method for controlling a start and stop of a counting episode on an automated cellular analyzer that uses liquid volumetric metering, the method comprising:
    a) providing to a metering tube a metering fluid composition comprising:
        i) a chelating agent,
        ii) an ionizing salt, and
        iii) a non-hemolytic surfactant present at a concentration of about 0.1 g/L to about 3.0 g/L;
        wherein the composition is non-hemolytic, has a pH of about 6.5 to about 7.5, and wherein the surface tension of the composition is between about 40 dynes/cm and about 66 dynes/cm; and
    b) flowing the metering fluid composition through the metering tube; wherein a meniscus of the metering fluid first triggers a start sensor, beginning the counting episode, and then triggers an end sensor, stopping the counting episode.

2. The method of claim 1, wherein the surface tension of the composition is between about 47 dynes/cm and about 64 dynes/cm.

3. The method of claim 1, wherein the surface tension of the composition is between about 52 dynes/cm and about 62 dynes/cm.

4. The method of claim 1, further comprising the step of placing the metering fluid composition in fluid communication with a sample bath.

5. The method of claim 1, wherein the ionizing salt is an alkaline metal chloride.

6. The method of claim 5, wherein the alkaline metal chloride is sodium chloride, potassium chloride, or combinations thereof.

7. The method of claim 1, wherein the composition further comprises a stabilizing ion.

8. The method of claim 7, wherein the stabilizing ion is an alkaline metal sulfate.

9. The method of claim 8, wherein the alkaline metal sulfate is sodium sulfate, potassium sulfate, or combinations thereof.

10. The method of claim 1, wherein the non-hemolytic surfactant is polyethoxylated nonyl phenol, polyoxyethylene 9 lauryl ether, ethoxylated glycol ether, ethoxylated monododecyl ether, ethoxylated dimethylsiloxane, dodecyl nonaethylene glycol ether, or combinations thereof.

11. The method of claim 1, wherein the composition further comprises one or more antimicrobial agents.

12. The method of claim 11, wherein the antimicrobial is 1,2-benzisothiazolin-3-one, 5-chloro-2-methyl-4-isothiazolin-3-one, 2-methyl-4-isothiazolin-3-one, 4-butylaminobenzoicacid-2-(dimethyl amino) ethylester hydrochloride, 5-bromo-5-nitro-1,3-dioxane, 1,2 dibromo-2,4 dicyanobutane, or combinations thereof.

13. The method of claim 1, wherein the composition is in a container configured to be connected to the automated cellular analyzer.

* * * * *